(12) United States Patent
Hawkins et al.

(10) Patent No.: US 12,318,774 B2
(45) Date of Patent: *Jun. 3, 2025

(54) MICROFLUIDIC DEVICE AND METHOD OF MANUFACTURING THE SAME

(71) Applicant: Truvian Sciences, Inc., San Diego, CA (US)

(72) Inventors: Jeff Hawkins, San Diego, CA (US); Ian Kleinemolen, San Diego, CA (US); Florence Lee, San Diego, CA (US); Matthew Tyson Grant, San Diego, CA (US); Dena Marrinucci, San Diego, CA (US); Xiaodong Zhao, San Diego, CA (US)

(73) Assignee: Truvian Sciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/940,111

(22) Filed: Nov. 7, 2024

(65) Prior Publication Data

US 2025/0065323 A1 Feb. 27, 2025

Related U.S. Application Data

(63) Continuation of application No. 18/539,226, filed on Dec. 13, 2023, now Pat. No. 12,172,158, which is a continuation of application No. PCT/US2022/034722, filed on Jun. 23, 2022.

(60) Provisional application No. 63/214,615, filed on Jun. 24, 2021.

(51) Int. Cl.
*B01L 3/00* (2006.01)

(52) U.S. Cl.
CPC . *B01L 3/502707* (2013.01); *B01L 2300/0645* (2013.01); *B01L 2300/0887* (2013.01)

(58) Field of Classification Search
CPC ....... B01L 3/502707; B01L 2300/0645; B01L 2300/0887
See application file for complete search history.

(56) References Cited

U.S. PATENT DOCUMENTS

| | | |
|---|---|---|
| 2005/0272142 A1 | 12/2005 | Horita |
| 2011/0038767 A1* | 2/2011 | Baril ................. B29C 66/73171 156/277 |
| 2013/0002753 A1 | 1/2013 | Wang et al. |
| 2015/0132753 A1 | 5/2015 | Ye et al. |

OTHER PUBLICATIONS

Gale et al., "A review of current Methods in Microfluidic device fabrications and Future commercialization prospects," 3(60): pp. 1-25 (2018).
Hawkins, "Rethinking the Clinical Laboratory Test Value Chain: Using New Technologies and New Approaches to Lower Costs, Speed Time-to-Answer, and Contribute to Improved Patient Outcomes," Truvian Slide Deck pp. 1-19 (Apr. 27, 2021).
Kratz et al., "Characterization of four functional biocompatible pressure-sensitive adhesives for rapid prototyping of cell-based lab-on-a-chip and organ-on-a-chip systems," Sci Rep 9, 9287 (2019) https://doi.org/10.1038/s41598-019-45633-x.
Theranos' Elizabeth Holmes Speaks at AACC Meeting. "Theranos Science & Technology: The Miniaturization of Laboratory Testing," American Association for Clinical Chemistry [Video] [Screen captures from video retrieved on the Internet at URL: https://www.mpo-mag.com/contents/view_videos/2016-08-02/theranos-elizabeth-holmes-speaks-at-aacc-meeting/] pp. 1-6 (Aug. 2, 2016).
WO: International Preliminary Report on Patentability for PCT/US2022/034722 mailed Jan. 10, 2024; 6 pages.
WO: International Search Report and Written Opinion for PCT/US2022/034722 dated Sep. 21, 2022; 7 pages.
CA: Office Action in CA Application No. 3223766 dated Jan. 31, 2025 (4 pages).

* cited by examiner

*Primary Examiner* — Narayan K Bhat
(74) *Attorney, Agent, or Firm* — Snell & Wilmer, L.L.P.; April Wurster (57) ABSTRACT

A method of manufacturing a laminate microfluidic device is described herein. Also described is the microfluidic device manufactured via the method of the disclosure, as well as use of the device to perform an assay. The laminate device includes a substrate layer, an adhesive layer having a cured adhesive with one or more channels or recesses formed therein, and a top layer.

20 Claims, 7 Drawing Sheets

MICROFLUIDIC DEVICE AND METHOD OF MANUFACTURING THE SAME

CROSS-REFERENCE TO RELATED APPLICATIONS

This application is a continuation application of U.S. application Ser. No. 18/539,226, filed Dec. 13, 2023, which is a continuation under 35 U.S.C. § 111 (a) on International Patent Application Serial No. PCT/US2022/034722, filed Jun. 23, 2022, which claims benefit of priority under 35 U.S.C. § 119 (e) of U.S. Provisional Patent Application Ser. No. 63/214,615, filed Jun. 24, 2021. The disclosure of the prior application is considered part of and is incorporated by reference in the disclosure of this application.

FIELD OF THE INVENTION

The present disclosure relates generally to analytic devices, and more particularly to a laminate microfluidic device, a method of manufacturing such a device, as well as a method of using the device to perform an assay.

BACKGROUND INFORMATION

Microfluidic devices are typically constructed via one or a combination of different conventional fabrication techniques. For example, substrates can be covered and patterned with photoresist, masked/exposed, etched, stripped, and then bonded with a cover layer. In another method, devices are comprised of stacks of laser cut and coated layers, which are assembled to create 3D microfluidic structures. Several other techniques exist using one or a combination of fabrication methods, such as polydimethylsiloxane (PDMS) and thermoset polyester (TPE) devices by replica molding, and fabrication of plastic devices using embossing, injection molding, and laser ablation.

Conventional methods for manufacturing precision microfluidic device are costly and involve highly variable bonding techniques. There remains a need for less costly and complex methods of producing precision microfluidic devices that produce reliable and repeatable assay results, and which may be adapted to detect any of a variety of analytes.

SUMMARY OF THE INVENTION

The present disclosure provides a method of manufacturing a laminate microfluidic device, as well as a device manufactured by such a method and method use thereof to perform an assay to detect an analyte.

Accordingly, in one embodiment, the disclosure provides a method of manufacturing a laminate microfluidic device.

In one aspect, the method includes: providing a substrate layer; providing an adhesive layer having a curable adhesive; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein curing comprises treating the composite laminate to promote curing of the curable adhesive causing transition of the adhesive layer to a stable and uniform thickness, and wherein the cured adhesive layer has a stable and uniform thickness across an entire width and length of the device. In various aspects, the stable and uniform thickness of the device as a whole or at least the adhesive layer, has a thickness deviation of equal to or less than about 5, 4, 3, 2 or 1 µm.

In another aspect, the method includes: providing a substrate layer; providing an adhesive layer having a curable adhesive; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein bonding comprises applying external pressure to the composite laminate, wherein curing comprises treating the composite laminate to promote curing of the curable adhesive causing transition of the adhesive layer to a stable and uniform thickness, and wherein the cured adhesive layer has a stable and uniform thickness across an entire width and length of the device. In various aspects, the stable and uniform thickness of the device as a whole or at least the adhesive layer, has a thickness deviation of equal to or less than about 5, 4, 3, 2 or 1 µm.

In another aspect, the method includes: providing a substrate layer; providing an adhesive layer having a curable adhesive, the adhesive layer having a first thickness; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein bonding comprises applying external pressure to the composite laminate, and wherein the adhesive layer of the composite laminate has a second thickness different than the first thickness; and curing the composite laminate to form the microfluidic device, wherein curing comprises treating the composite laminate to promote curing of the curable adhesive causing transition of the adhesive layer from the second thickness to a stable and uniform third thickness, and wherein the cured adhesive layer has a stable and uniform thickness across an entire width and length of the device. In various aspects, the stable and uniform thickness of the device as a whole or at least the adhesive layer, has a thickness deviation of equal to or less than about 5, 4, 3, 2 or 1 µm.

In yet another aspect, the method includes: providing a substrate layer; providing an adhesive layer having a curable adhesive including a polymerizable monomer, the adhesive layer having a first thickness; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein bonding optionally comprises applying external pressure to the composite laminate, and wherein the adhesive layer of the composite laminate has a second thickness different than the first thickness; and curing the composite laminate to form the microfluidic device, wherein curing comprises treating the composite laminate to promote polymerization of the monomer causing transition of the adhesive layer from the second thickness to a stable and uniform third thickness, and wherein the cured adhesive layer has a stable and uniform thickness across an entire width and length of the device. In various aspects, the stable and uniform thickness of the device as a whole or at least the adhesive layer, has a thickness deviation of equal to or less than about 5, 4, 3, 2 or 1 µm.

In still another aspect, the method includes: providing a substrate layer; providing an adhesive layer having a curable adhesive including a polymerizable monomer, the adhesive layer having a first thickness; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein bonding comprises applying external pressure to the composite laminate, and wherein the adhesive layer of the composite laminate has a second reduced thickness less than the first thickness; and curing the composite laminate to form the microfluidic device, wherein curing comprises treating the composite laminate to promote polymerization of the monomer causing transition of the adhesive layer from the second reduced thickness to a stable and uniform third thickness, and wherein the cured adhesive layer has a stable and uniform thickness across an entire width and length of the device. In various aspects, the stable and uniform thickness of the device has a thickness deviation of equal to or less than about 5, 4, 3, 2 or 1 µm.

In another embodiment, the disclosure provides a method of performing an assay using the laminate microfluidic device of the disclosure. The method includes: providing the laminate microfluidic device of any preceding claim; and performing an assay using the laminate microfluidic device to detect an analyte in a liquid sample, thereby performing an assay.

In still another embodiment, the disclosure provides a laminate microfluidic device manufactured by the method described herein. In various aspects, the stable and uniform thickness of the device has a thickness deviation of equal to or less than about 5, 4, 3, 2 or 1 µm.

DETAILED DESCRIPTION OF THE INVENTION

The disclosure provides a method of manufacturing a laminate microfluidic device. The method described herein permits the production of a high precision microfluidic device via low-cost means of manufacture.

Frequently, production of comparable microfluidic devices, or chips, requires conventional high precision injection molding or machining and challenging bonding techniques. Typical production methods are especially capital intensive to produce/mold accurately, require device-based features such as positive displacement or pumping techniques to fill reliably, lack dimensional repeatability to support volumetric based analysis techniques, employ high cost or highly variable bonding techniques, and/or have severe lifetime limitations due to temperamental coatings.

The method of the disclosure produces a microfluidic device having stable and uniform dimensions within acceptable tolerances that are required of such devices, especially for use in biological or chemical assays to detect an analyte of interest. The microfluidic device generated by the method of the disclosure is produced at a lower cost than conventional manufacturing techniques while maintaining stable and uniform structural dimensions within an acceptable tolerance. The advantages of stable and uniform structural dimensions are most evident in microfluidic devices having a planar geometry in which channel height dimensions must be strictly controlled to allow uniform flow of fluid and analyte within the channel to conduct a viable analyte detection assay. For example, typical volumetric measurements of a fluid passing through a fluidic channel require a uniform height deviation across the one or more channels of less than +/−1 to 5 µm, and a desirable uniform height deviation of +/−1 to 2 µm or less. The uniform height requirement is especially true in quantification assays utilizing whole cells.

Before the present compositions and methods are described, it is to be understood that this invention is not limited to particular assemblies, methods and experimental conditions described, as such assemblies, methods, and conditions may vary. It is also to be understood that the terminology used herein is for purposes of describing particular embodiments and/or aspects only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the device" or "the method" includes one or more devices, methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, the word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Accordingly, in one embodiment, the disclosure provides a method of manufacturing a laminate microfluidic device.

In one aspect, the method includes: providing a substrate layer; providing an adhesive layer having a curable adhesive; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein curing comprises treating the composite laminate to promote curing of the curable adhesive causing transition of the adhesive layer to a stable and uniform thickness, and wherein the cured adhesive layer has a stable and uniform thickness across an entire width and length of the device. In various aspects, the stable and uniform thickness of the device as a whole or at least the adhesive layer, has a thickness deviation of equal to or less than about 5, 4, 3, 2 or 1 μm.

In another aspect, the method includes: providing a substrate layer; providing an adhesive layer having a curable adhesive including a polymerizable monomer, the adhesive layer having a first thickness; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein bonding optionally comprises applying external pressure to the composite laminate, and wherein the adhesive layer of the composite laminate has a second thickness different than the first thickness; and curing the composite laminate to form the microfluidic device, wherein curing comprises treating the composite laminate to promote polymerization of the monomer causing transition of the adhesive layer from the second thickness to a stable and uniform third thickness, and wherein the cured adhesive layer has a stable and uniform thickness across an entire width and length of the device. In various aspects, the stable and uniform thickness of the device as a whole or at least the adhesive layer, has a thickness deviation of equal to or less than about 5, 4, 3, 2 or 1 μm.

In another aspect, the method includes: providing a substrate layer; providing an adhesive layer having a curable adhesive including a polymerizable monomer, the adhesive layer having a first thickness; providing a top layer; forming at least one channel or recess feature in the adhesive layer; laminating the adhesive layer and the top layer together thereby forming an intermediate laminate; bonding the intermediate laminate to the substrate layer thereby forming a composite laminate, wherein bonding comprises applying external pressure to the composite laminate, and wherein the adhesive layer of the composite laminate has a second reduced thickness less than the first thickness; and curing the composite laminate to form the microfluidic device, wherein curing comprises treating the composite laminate to promote polymerization of the monomer causing transition of the adhesive layer from the second reduced thickness to a stable and uniform third thickness, and wherein the cured adhesive layer has a stable and uniform thickness across an entire width and length of the device.

An illustrative example of a laminate microfluidic device produced by the method described herein is also provided. With reference to FIGS. 1-6, the device 10 includes a substrate layer 20, a top layer 30 and an intermediate adhesive layer 40. In various aspects, the device 10 includes at least one flow channel 50 (or other recess feature defined by a void of adhesive material between the substrate layer and top layer).

In various aspects, rather than molding or machining a channel structure into a substrate, the method of the disclosure describes use of a multilayer construction, e.g., three or more layer laminate. In some aspects, a flat (low cost, simple to manufacture) substrate layer is combined with an adhesive layer (e.g., a pressure-sensitive adhesive or transfer adhesive having a channel structure or other feature cut into the adhesive layer), and a top layer (e.g., a thin film). As discussed herein, the manufacturing methodology of the present disclosure yields very high thickness repeatability on the scale of typical microfluidic devices. In addition, processes for cutting a channel structure or feature into planar substrates are low cost (e.g., laser cutting at prototype scale, rotary die cutting/web conversion at production scale). Further, laminating planar layers, particularly with a pressure-sensitive adhesive or transfer adhesive, can be conducted as an extension of the cutting process (e.g., web conversion). As such, the laminate microfluidic structure of the disclosure yields a high precision structure from a channel shape and height standpoint for very low cost.

This methodology of the disclosure, optionally combined with functionalized coatings, e.g., hydrophilic coatings, yields a microfluidic device that allows for passive fluid transport and high precision geometry, which is instrumental to volume-based calculations and analysis required for biological and chemical assays.

As discussed herein, in some aspects of the disclosure, feature patterns (e.g., channels or other recess features) are cut into a pressure-sensitive adhesive layer using any convention technique known in the art, for example, by laser cutting, die cutting, rotary die cutting, press cutting, knife plotters and the like. The adhesive layer is used to form a laminate including a substrate layer and top layer to form the microfluidic device.

In some aspects, the substrate layer and top layer are polycarbonate materials and the adhesive layer is formed from a pressure-sensitive adhesive. In some aspects, the adhesive layer has a cutting pattern that is easily reproduced via a variety of cutting techniques, e.g., laser cutting may be utilized to facilitate prototyping and design variation without the need for tooling; and rotary die cutting may be used for high output and low cost production (multiple laminated devices can be produced per second on common web converting equipment).

While the present disclosure illustrates a microfluidic device having three layers, it will be appreciated that the device may include more than three layers and include any number of adhesive layers interposed between adjacent non-adhesive layers. Also, it will be appreciated that individual adhesive layers need not be separated by an adjacent non-adhesive layer but rather the device may include 1, 2, 3, 4, 5, 6 or more adhesive layers laminated directs to one another. Similarly, in some aspects, non-adhesive layers need not include an interposed adhesive layer and may be bonded together using a bonding technique known in the art, e.g., laser bonding, laminating, ultrasonic bonding, thermal bonding, solvent bonding, or adhesive bonding. In some aspects, a thermal bonding process not inconsistent with the objectives of the present disclosure can be used to bond non-adhesive layers. Non-limiting examples include laser welding, thermal fusion bonding, and ultrasonic welding.

In various aspects, the device includes any number of adhesive layers and non-adhesive layers, in any structural combination. In one aspect, the device includes a single adhesive layer interposed between two non-adhesive layers. In one aspect, the device includes a single adhesive layer interposed between 2, 3, 4, 5, 6 or more non-adhesive layers. In one aspect, the device includes 2, 3, 4, 5, 6 or more adhesive layers interposed between two non-adhesive layers. In one aspect, the device includes 2 adhesive layers, each layer being interposed between non-adhesive layers. In one aspect, the device includes 3 adhesive layers, each layer being interposed between non-adhesive layers. In one aspect, the device includes 3 adhesive layers, wherein 2 of the adhesive layers are laminated directly to each other and separated from the third adhesive layer by an interposed non-adhesive layer. In one aspect, the device includes 4 adhesive layers, wherein 2 of the adhesive layers are laminated directly to each other and separated from the other 2 adhesive layers that are laminated directly to each other by an interposed non-adhesive layer. In one aspect, the device includes 4 adhesive layers, wherein 3 of the adhesive layers are laminated directly to each other and separated from the fourth adhesive layer by an interposed non-adhesive layer.

In various aspects, the substrate layer and the top layer are formed of a material that is the same or different. There are several material types that may be utilized to form the substrate layer and/or the top layer. In various aspects, the layers are composed of a single material, composite materials, multiple materials, multilayer of materials, alloys, or a combination thereof. In some aspects, the material for use in forming the layers includes an inorganic material, an organic material, or a mix. Examples of inorganic materials for the substrate layer and/or the top layer include, but are not limited to, glass, quartz, oxides, silicon, silicon-dioxide, silicon-nitride, hafnium oxide (HfO), aluminum oxide (AlO), semiconductors: (silicon, GaAs, GaN, and the like), metals (e.g., gold, silver, copper, aluminum, Ti, Ni, and the like), ceramics, or any combinations of thereof. Examples of organic materials for the substrate layer and/or the top layer include, but are not limited to, polymers (e.g., plastics) or amorphous organic materials. In some aspects, the substrate layer and/or the top layer is composed of a rigid or semi-rigid gel.

In certain aspects, the substrate layer and/or the top layer are made from any suitable plastic not inconsistent with the objectives of the present disclosure. In some aspects, the substrate layer and/or the top layer are composed of acrylate polymers, vinyl polymers, olefin polymers, cellulosic polymers, noncellulosic polymers, polyester polymers, Nylon, polypropylene, polyvinylbutyrale, polyamide, polyamide 12, polyarylate, parylene, polyether ether ketone, polybenzimidazole, polyamide-imide, thermoplastic polyimide, liquid crystal polymer (such as Kevlar™, Vectran™ and Zenite™), polyphthalamide, polycarbonate, polystyrene, polysulfone, polyimide, polyphenolsulfone, polyetherimide, polyether sulfone, polyarylethersulfone, poly (bisphenol-A sulfone), polyarylene sulfone, polyethylene, polyester, vinyl, poly (vinylchloride) (PVC), polyurethane, polyvinylidene chloride, cyclic olefin polymer (COP), cyclic olefin copolymer (COC), polycarbonate-polyethylene terephthalate-blends, polycarbonatepolybutylene terephthalate-blends, polycarbonate-acrylnitrile/styrene/acrylnitrile-copolymer-blends, polycarbonate-acrylnitrile/butadiene/styrene-copolymer-blends, polymethylmethacrylate-acrylnitrile/butadiene/styrene-copolymer-blends (MABS), polyethylene terephthalate, polybutylene terephthalate, polymethylmethacrylate, polybutylacrylate, polymethylmethacrylate-polyvinylidenedifluoride-blends, acrylnitrile/butadiene/styrene-copolymere (ABS), styrene/acrylnitrile-copolymere (SAN), Victrex™ HTA, polyphenylenesulfone, polydimethylsiloxane (PDMS), rubber, or any combination thereof. In some aspects, the substrate layer and/or the top layer include acrylate polymers, vinyl polymers, olefin polymers, cellulosic polymers, noncellulosic polymers, polyester polymers, Nylon, cyclic olefin copolymer (COC), poly (methyl methacrylate) (PMMA), polycarbonate (PC), cyclic olefin polymer (COP), liquid crystalline polymer (LCP), polyamide (PA), polyethylene (PE), polyimide (PI), polypropylene (PP), poly (phenylene ether) (PPE), polystyrene (PS), polyoxymethylene (POM), polyether ether ketone (PEEK), polyether sulfone (PES), poly (ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFA), polydimethylsiloxane (PDMS), rubber, or any combination of thereof.

It will be apparent that the method of the disclosure is applicable to virtually any substrate and top layer material, depending on desired functionality, such as optical or electrically conductive functionality. In addition, the substrate and top layer material do not need to be homogeneous in construction. For example, a layer could have a substrate material and one, or a multitude, of continuous or interrupted/patterned coatings, such as functionalized coatings or electrically conductive coatings. In some aspects, the method may utilize a layer having electrically conductive material or electronic circuitry, such as a semiconductor with active electrical or mechanical structures that serve to pump, gate, excite, or otherwise actively manipulate a fluid introduced to the fluidic device. In some aspects, a layer may be a printed circuit board, or in electrical connection with a printed circuit board. In some aspects, a layer may include one or more electrodes or sensors, optionally in connection with other electronic circuitry operable to detect an analyte via any number of means known in the art, including changes in electrical conductivity or resistivity, optical properties (e.g., fluorescence, absorbance and the like), a chemical reaction, magnetic interaction, analyte/conjugate binding and the like.

In various aspects, the substrate layer and/or the top layer, or portions thereof, may be formed from a material which is compatible with biological material and/or molecules (e.g., biocompatible), such as cells or cellular components (e.g., nuclei, perinuclear compartments, nuclear membranes, mitochondria, chloroplasts, or cell membranes), proteins (e.g., antibodies, or membrane, trans-membrane or cytosolic proteins), oligonucleotides, lipids, polysaccharides, nucleic acids, viral particles, ribosomes, hormones, ions or cofactors.

In one aspect, the substrate layer and the top layer include a polycarbonate.

In various aspects, the thickness of the substrate layer and/or the top layer are not particularly limited. However, in some aspects, the thickness is about 10 μm to about 10,000 μm including for example, about 50 μm to about 9,000 μm, about 50 μm to about 8,000 μm, about 50 μm to about 7,000 μm, about 50 μm to about 6,000 μm, about 50 μm to about 5,000 μm, about 50 μm to about 4,000 μm, about 50 μm to about 3,000 μm, about 50 μm to about 2,000 μm, about about 50 μm to about 1,000 μm. In some aspects, the thickness is about 10 μm to about 1,000 μm including for example, about 50 μm to about 500 μm, about 50 μm to about 250 μm, and about 50 μm to about 200 μm.

There are several material types that may be utilized to form the adhesive layer which are curable. As used herein, the terms "cure," "curing" and "curable" refer to a process of treating a material to induce transformation of the material into a stabilized layer of uniform thickness while the term "cured" refers to a material treated by such a process.

As used herein, the terms "stable" and "stabilized" refer to a material that maintains dimensional stability. In various aspects, the cured adhesive layer remains stable for at least about, or greater than about 1, about 2, about 3, about 4, about, 5, about 6, about 7, about 8, about 9, about 10, about 15, about 20, about 50, or about 100 or more years.

In various aspects, the adhesive layer is formed of a single material or a composite material. In some aspects, the adhesive layer may be formed from two or more individual adhesive layers, each layer being of the same or different material.

In some aspects, the material for use in forming the adhesive layer includes a silicone, cyanoacrylate, urethane, acrylic, epoxy or thermoplastic adhesive. In some aspects, the adhesive layer contains a polymer adhesive or a non-polymer adhesive. In some aspects, the adhesive layer contains an animal product, acrylate, acrylic, copper, epoxy, graphite, milk, nickel, nylon, polyester, acrylic, oil, polyurethane, rubber/latex, silicone, silver, starch or water. In some aspects, the adhesive layer is an anaerobic, resin, bismaleimide, casein, cyanoacrylate, dextrin, electrically conductive, hot melt, phenolic, plastisol, polyvinyl acetate, reactive, solvent-based, thermoset, UV curing or water-based adhesive.

In various aspects, curing includes treating the adhesive with heat, light, pressure, sound (e.g., ultrasound), ionizing radiation, moisture, and/or a chemical.

In some aspects, the adhesive layer is composed of an adhesive that includes a base monomer that is capable of polymerization into a polymer by curing the adhesive. In some aspects, curing includes treating the adhesive with a process to promote polymerization of the base monomer causing the adhesive to reach a maximally stable mechanical state, which may be accomplished via treating the adhesive with heat, light, pressure, sound (e.g., ultrasound), radiation, moisture, and/or a chemical.

In addition to providing a less complex, low-cost manufacturing method, the method of the disclosure provides a method of manufacturing a device having dimensional stability and repeatability of manufacture. A typical lamination process can cause temporary deformation and/or thickness compression of one or more of the laminate layers, such as the adhesive layer. In various aspects, the temporary deformation and/or thickness compression can be more quickly remediated via the application of a curing process as described above, such as exposure to elevated temperature and/or controlled atmosphere. The curing process results in accelerated normalization and dimensional stability by accelerating the monomer to polymer transformation of the adhesive layer.

In various aspects, curing includes heat treatment of the composed laminate which includes subjecting the adhesive layer to an elevated temperature for a duration of time. In some aspects, the elevated temperature is greater than about 25, 30, 35, 40, 45 or 55° C., including about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60° C. In some aspects, the adhesive layer is subjected to the elevated temperature for at least about 24 hours and less than about 36 hours. In some aspects, the adhesive layer is subjected to the elevated temperature for less than about 24, 20, 16, 12, 8 or 4 hours.

In some aspects, the adhesive layer is a pressure-sensitive adhesive layer. The pressure-sensitive adhesive that is used to form the adhesive layer is not especially limited. Examples include a general pressure-sensitive adhesive such as an acrylic, cyanoacrylate, silicone, or rubber-based pressure-sensitive adhesive. For some aspects, as the pressure-sensitive adhesive, an acrylic pressure-sensitive adhesive having a base acrylic monomer that may be polymerized into an acrylic polymer is utilized.

Examples of the acrylic polymer include acrylic polymers using, as a monomer component, one or more types of (meth)acrylic acid alkyl esters (for example, a straight chain or branched chain alkyl ester having 1 to 30 carbon atoms, and particularly 4 to 18 carbon atoms in the alkyl group such as methylester, ethylester, propylester, isopropylester, butylester, isobutylester, sec-butylester, t-butylester, pentylester, isopentylester, hexylester, heptylester, octylester, 2-ethylhexylester, isooctylester, nonylester, decylester, isodecylester, undecylester, dodecylester, tridecylester, tetradecylester, hexadecylester, octadecylester, and eicosylester) and (meth)acrylic acid cycloalkyl esters (for example, cyclopentylester, cyclohexylester, and the like). The (meth)acrylic acid ester means an acrylic acid ester and/or a methacrylic acid ester and has the very same meaning as (meth) in the present disclosure.

The acrylic polymer may optionally contain a unit corresponding to a different monomer component copolymerizable with the above-mentioned alkyl ester of (meth)acrylic acid or cycloalkyl ester thereof in order to improve the cohesive force, heat resistance or some other property of the polymer. Examples of such a monomer component include carboxyl-containing monomers such as acrylic acid, methacrylic acid, carboxyethyl (meth)acrylate, carboxypentyl (meth)acrylate, itaconic acid, maleic acid, fumaric acid, and crotonic acid; acid anhydride monomers such as maleic anhydride, and itaconic anhydride; hydroxyl-containing monomers such as 2-hydroxyethyl (meth)acrylate, 2-hydroxypropyl (meth)acrylate, 4-hydroxybutyl (meth)acrylate, 6-hydroxyhexyl (meth)acrylate, 8-hydroxyoctyl (meth)acrylate, 10-hydroxydecyl (meth)acrylate, 12-hydroxylauryl (meth)acrylate, and (4-hydroxylmethylcyclohexyl) methyl (meth)acrylate; sulfonic acid group containing monomers such as styrenesulfonic acid, allylsulfonic acid, 2-(meth)acrylamide-2-methylpropanesulfonic acid, (meth)acrylamidepropanesulfonic acid, sulfopropyl (meth)acrylate, and (meth) acryloyloxynaphthalenesulfonic acid; phosphoric acid group containing monomers such as 2-hydroxyethylacryloyl phosphate; acrylamide; and acrylonitrile. These copolymerizable monomer components may be used alone or in combination of two or more thereof. The amount of the copolymerizable monomer(s) to be used is about 40% or less by weight of all the monomer components.

For crosslinking, the acrylic polymer can also contain multifunctional monomers if necessary, as the copolymerizable monomer component. Such multifunctional monomers include hexane diol di(meth)acrylate, (poly)ethylene glycol di(meth)acrylate, (poly) propylene glycol di(meth) acrylate, neopentyl glycol di(meth)acrylate, pentaerythritol di(meth)acrylate, trimethylol propane tri(meth)acrylate, pentaerythritol tri(meth)acrylate, dipentaerythritol hexa(meth)acrylate, epoxy (meth)acrylate, polyester (meth)acrylate, urethane (meth)acrylate, and the like. These multifunctional monomers can also be used as a mixture of one or more thereof. From the viewpoint of adhesiveness, the use amount of the multifunctional monomer is about 30 wt % or less based on the whole monomer components.

In some aspects, the adhesive includes an epoxy resin including one more of: polyglycidyl ether compounds of mononuclear polyhydric phenol compounds, such as hydroquinone, resorcin, pyrocatechol, phloroglucinol, and the like; polyglycidyl ethers of polyols, such as ethylene glycol, propylene glycol, butylene glycol, hexanediol, polyglycol, thiodiglycol, glycerin, trimethylol propane, pentaerythritol, sorbitol, bisphenol A-alkylene oxide adduct, and the like; glycidyl esters of aliphatic, aromatic or alicyclic polybasic acids, such as maleic acid, fumaric acid, itaconic acid, succinic acid, glutaric acid, suberic acid, adipic acid, azelaic acid, sebacic acid, dimer acid, trimer acid, phthalic acid, isophthalic acid, terephthalic acid, trimellitic acid, trimesic acid, pyromellitic acid, tetrahydrophthalic acid, hexahydrophthalic acid, endomethylene tetrahydrophthalic acid, and the like; homopolymers or copolymers of glycidyl methacrylate; epoxidized products of cyclic olefin compounds, such as vinylcyclohexene diepoxide, dicyclopentanediene diepoxide, 3,4-epoxycyclohexylmethyl-3,4-epoxycyclohexane carboxylate, 3,4-epoxy-6-methylcyclohexylmethyl-6-methylcyclohexane carboxylate, bis(3,4-epoxy-6-methylcyclohexylmethyl) adipate, and the like; epoxidized conjugated diene polymers, such as epoxidized polybutadiene, epoxidized styrene-butadiene copolymer, and the like; and heterocyclic compounds, such as triglycidyl isocyanurate, and the like. These epoxy resins may be internally crosslinked by isocyanate-terminal prepolymers, or highly polymerized by using multivalent active hydrogen compounds (polyhydric phenol, polyamines, carbonyl group-containing compounds, polyphosphoric esters, and the like).

In some aspects, the adhesive includes a radical-polymerizable compound including one more of: N-alkyl group-containing (meth)acrylic amide derivatives, such as N-methyl (meth)acrylic amide, N,N-dimethyl (meth)acrylic amide, N,N-diethyl (meth)acrylic amide, N-isopropyl (meth)acrylic amide, N-butyl (meth)acrylic amide, N-hexyl (meth)acrylic amide, and the like; (meth)acrylic amide derivatives, such as N-methylol (meth)acrylic amide, N-hydroxyethyl (meth)acrylic amide, N-methylol-N-propane (meth)acrylic amide, N-alkoxy group-containing (meth) acrylic amide derivatives such as N-methoxymethylacrylamide and N-ethoxymethylacrylamide, N-acryloylmorpholine, N-acryloylpiperidine, N-methacryloylpiperidine, N-acryloylpyrrolidine, and the like; unsaturated aliphatic hydrocarbons, such as ethylene, propylene, butylene, isobutylene, vinyl chloride, vinylidene chloride, vinylidene fluoride, and tetrafluoroethylene; (meth)acrylic acid, .alpha.-chloroacrylic acid, itaconic acid, maleic acid, citraconic acid, fumaric acid, hymic acid, crotonic acid, isocrotonic acid, vinylacetic acid, allylacetic acid, cinnamic acid, sorbic acid, mesaconic acid, mono[2-(meth) acryloyloxyethyl] succinate, mono[2-(meth) acryloyloxyethyl] phthalate, a mono(meth)acrylate of a polymer having a carboxy group and a hydroxyl group at both ends, such as .omega.-carboxypolycaprolactone mono(meth)acrylate; hydroxyethyl (meth)acrylate-maleate, hydroxypropyl (meth)acrylate-maleate, dicyclopentadiene-maleate, unsaturated polybasic acids such as a polyfunctional (meth)acrylate having one carboxyl group and two or more (meth) acryloyl groups; 2-hydroxyethyl (meth)acrylate, 2-hydroxypropyl (meth)acrylate, glycidyl (meth)acrylate, Acrylic Compounds Nos. 1 to 4 shown below, methyl (meth)acrylate, butyl (meth)acrylate, isobutyl (meth)acrylate, t-butyl (meth)acrylate, cyclohexyl (meth)acrylate, n-octyl (meth) acrylate, isooctyl (meth)acrylate, isononyl (meth)acrylate, stearyl (meth)acrylate, lauryl (meth)acrylate, methoxyethyl (meth)acrylate, dimethylaminomethyl (meth)acrylate, dimethylaminoethyl (meth)acrylate, aminopropyl (meth)acrylate, dimethylaminopropyl (meth)acrylate, ethoxyethyl (meth)acrylate, poly (ethoxy)ethyl (meth)acrylate, butoxyethoxyethyl (meth)acrylate, ethylhexyl (meth)acrylate, phenoxyethyl (meth)acrylate, tetrahydrofuryl (meth)acrylate, vinyl (meth)acrylate, allyl (meth)acrylate, benzyl (meth) acrylate; esters between an unsaturated monobasic acid and a polyhydric alcohol or polyhydric phenol, such as ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri(meth)acrylate, dipentaerythritol hexa(meth)acrylate, dipentaerythritol penta(meth)acrylate, pentaerythritol tetra (meth)acrylate, pentaerythritol tri(meth)acrylate, tricyclodecanedimethylol di(meth)acrylate, tri[(meth) acryloylethyl] isocyanurate, and polyester (meth)acrylate oligomers; metal salts of unsaturated polybasic acids, such as zinc (meth) acrylate and magnesium (meth)acrylate; unsaturated polybasic acid anhydrides, such as maleic anhydride, itaconic anhydride, citraconic anhydride, methyltetrahydrophthalic anhydride, tetrahydrophthalic anhydride, trialkyltetrahydrophthalic anhydrides, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride; unsaturated aldehydes, such as acrolein; unsaturated nitriles, such as (meth) acrylonitrile, .alpha.-chloroacrylonitrile, vinylidene cyanide, and allyl cyanide; unsaturated aromatic compounds, such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether, unsaturated ketones, such as methyl vinyl ketone; unsaturated amine compounds, such as vinylamine, allylamine, N-vinylpyrrolidone, and vinylpiperidine; vinyl alcohols, such as allyl alcohol and crotyl alcohol; vinyl ethers, such as vinyl methyl ether, vinyl ethyl ether, n-butyl vinyl ether, isobutyl vinyl ether, and allyl glycidyl ether, unsaturated imides, such as maleimide, N-phenylmaleimide, and N-cyclohexylmaleimide; indenes, such as indene and 1-methylindene; aliphatic conjugated dienes, such as 1,3-butadiene, isoprene, and chloroprene; macromonomers having a mono(meth)acryloyl group at the end of the polymeric molecular chain thereof, such as polystyrene, polymethyl (meth)acrylate, poly-n-butyl (meth)acrylate, and polysiloxanes; vinyl chloride, vinylidene chloride, divinyl succinate, diallyl phthalate, triallyl phosphate, triallyl isocyanurate, vinyl thioether, vinylimidazole, vinyloxazoline, vinylcarbazole, vinylpyrrolidone, vinylpyridine, vinylurethane compounds formed between a hydroxyl-containing vinyl monomer and a polyisocyanate compound, and vinylepoxy compounds formed between a hydroxyl-containing vinyl monomer and a polyepoxy compound.

In some aspects, the adhesive includes a thiol-based curing agent. The thiol-based curing agent may be used for curing a component of the adhesive by irradiation of light and/or by heating. Examples of the thiol-based curing agent may include polythiol compounds. Examples of polythiol compounds may include pentaerythritol tetrakis(3-mercaptopropionate), pentaerythritol tetrakis(thioglycolate), dipentaerythritol hexakis (3-mercaptopropionate), dipentaerythritol hexakis (3-mercaptobutyrate), 1,3,4,6-tetrakis(2-mercaptoethyl)-1,3,4,6-tetraazaoctahydropentalene-2,5-dione, 1,3,5-tris(3-mercaptopropyl)-1,3,5-triazine-2,4,6 (1H,3H,5H)-trione, 4-mercaptomethyl-1,8-dimercapto-3,6-dithiaoctane, 4,8-, 4,7- or 5,7-dimercaptomethyl-1,11-dimercapto-3,6,9-trithiaundecane, 1,3,4,6-tetrakis(2-mercaptoethyl)glycoluril, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1, 11-dimercapto-3,6,9-trithiaundecane, 4,7-dimercaptomethyl-1, 11-dimercapto-3,6,9-trithiaundecane, 4,8-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, 1,1,3,3-tetrakis(mercaptomethylthio)propane, 1, 1,2,2,2-tetrakis(mercaptomethylthio) ethane, 4,6-bis(mercaptomethylthio)-1,3-dithiane, 1, 1,5,5-tetrakis (mercaptomethylthio)-3-thiapentane, 1, 1,6,6-tetrakis(mercaptomethylthio)-3,4-dithiahexane, 2,2-bis(mercaptomethylthio) ethane thiol, 3-mercaptomethylthio-1,7-dimercapto-2,6-dithiaheptane, 3,6-bis(mercaptomethylthio)-1,9-dimercapto-2,5,8-trithianonane, 3-mercaptomethylthio-1,6-dimercapto-2,5-dithiahexane, 1,1,9,9-tetrakis (mercaptomethylthio)-5-(3,3-bis(mercaptomethylthio)-1-thi-apropyl)3,7-dithianonane, tris(2,2-bis (mercaptomethylthio)ethyl)methane, tris(4,4-bis (mercaptomethylthio)-2-thiabutyl)methane, tetrakis(2,2-bis (mercaptomethylthio)ethyl)methane, tetrakis(4,4-bis (mercaptomethylthio)-2-thiabutyl)methane, 3,5,9,11-tetrakis(mercaptomethylthio)-1,13-dimercapto-2,6,8,12-tetrathiat-ridecane, 3,5,9, 11, 15, 17-hexakis (mercaptomethylthio)-1,19-dimercapto-2,6,8-, 12,14,18-hexathianonadecane, 9-(2,2-bis(mercaptomethylthio)ethyl)-3,5,13,15-tetrakis(mercaptomethylthi-o)-1, 17-dimercapto-2,6,8, 10, 12, 16-hexathiaheptadecane, 3,4,8,9-tetrakis (mercaptomethylthio)-1,11-dimercapto-2,5,7,10-tetrathiaun-decane, 3,4,8,9,13,14-hexakis (mercaptomethylthio)-1, 16-dimercapto-2,5,7,10-,12,15-hexathiahexadecane, 8-[bis(mercaptomethylthio) methyl]-3, 4,12,13-tetrakis(mercaptomethylthio)-1,15-dimercapto-2,5, 7,9,11,14-hexathiapentadecane, 4,6-bis[3,5-bis (mercaptomethylthio)-7-mercapto-2,6-dithiaheptylthio]-1, 3-dithiane, 4-[3,5-bis(mercaptomethylthio)-7-mercapto-2,6-dithiaheptylthio]-6-mercaptomethylthio-1,3-dithiane, 1,1-bis[4-(6-mercaptomethylthio)-1,3-dithianylthio]-1,3-bis (mercaptomethy-lthio)propane, 1-[4-(6-mercaptomethylthio)-1,3-dithianylthio]-3-[2,2-bis (mercaptomethylt-hio)ethyl]-7,9-bis(mercaptomethylthio)-2,4,6,10-tetrathiaundecane, 1,5-bis[4-(6-mercaptomethylthio)-1,3-dithianylthio]-3-[2-(1,3-dithietanyl-)]methyl-2,4-dithiapentane, 3-[2-(1,3-dithietanyl)]methyl-7,9-bis(mercaptomethylthio)-1,11-dimercapto-2,4,6,10-tetrathiaundecane, 9-[2-(1,3-dithietanyl)]methyl-3,5,13,15-thetrakis (mercaptomethylthio)-1,17-dimercapto-2,6,8, 10, 12, 16-hexathiaheptadecane, 3-[2-(1,3-dithietanyl)]methyl-7,9, 13,15-tetrakis(mercaptomethylthio)-1,17-dimercapto-2,4,6, 10,12,16-hexathiaheptadecane, 3,7-bis[2-(1,3-dithietanyl)] methyl-1,9-dimercapto-2,4,6,8-tetrathianonane-, 4,6-bis {3-[2-(1,3-dithietanyl)]methyl-5-mercapto-2,4-dithiapentylthio}-1-,3-dithiane, 4,6-bis[4-(6-mercaptomethylthio)-1,3-dithianylthio]-6-[4-(6-mercaptomethy-lthio)-1,3-dithianylthio]-1,3-dithiane, 4-[3, 4,8,9-tetrakis(mercaptomethylthio)-11-mercapto-2,5,7, 10-tetrathiaund-ecyl]-5-mercaptomethylthio-1,3-dithiolane, 4,5-bis[3,4-bis(mercaptomethylthio)-6-mercapto-2,5-dithiahexylthio]-1,3-d-ithiolane, 4-[3,4-bis(mercaptomethylthio)-6-mercapto-2,5-dithiahexylthio]-5-mercaptomethylthio-1,3-dithiolane, 4-[3-bis(mercaptomethylthio) methyl-5,6-bis (mercaptomethylthio)-8-mercapto-2,4,7-trithiaoctyl]-5-mercaptomethylthio-1,3-dithiolane, 2-{bis[3,4-bis (mercaptomethylthio)-6-mercapto-2,5-dithiahexylthio] methyl}-1,3-dithietane, 2-[3,4-bis(mercaptomethylthio)-6-mercapto-2,5-dithiahexylthio] mercaptomet-hylthiomethyl-1,3-dithietane, 2-[3,4,8,9-tetrakis(mercaptomethylthio)-11-mercapto-2,5,7,10-tetrathiaund-ecylthio] mercaptomethylthiomethyl-1,3-dithietane, 2-[3-bis (mercaptomethylthio) methyl-5,6-bis(mercaptomethylthio)-8-mercapto-2,4,7-trithiaoctyl]mercaptomethylthiomethyl-1, 3-dithietane, 4,5-bis {1-[2-(1,3-dithietanyl)]-3-mercapto-2-thiapropylthio}-1,3-dithiola-ne, 4-{1-[2-(1,3-dithietanyl)]-3-mercapto-2-thiapropylthio}-5-[1,2-bis(mer-captomethylthio)-4-mercapto-3-thiabutylthio]-1,3-dithiolane, 2-{bis[4-(5-mercaptomethylthio-1,3-dithiolanyl) thio]methyl}-1,3-dithietan-e, 4-[4-(5-mercaptomethylthio-1,3-dithiolanyl) thio]-5-{1-[2-(1,3-dithietan-yl)]-3-mercapto-2-thiapropylthio}-1,3-dithiolane, and the like. In the present invention, one type of the aforementioned polythiol compound may be used singly, or two or more types may be used in combination.

In some aspects, the adhesive includes a hydrophobic monomer, for example, a hydrophobic (meth)acrylic obtained by using at least one selected from polyethylene glycol di(meth)acrylate, polyethylene glycol tri(meth)acrylate, polypropylene glycol di(meth)acrylate, polypropylene glycol tri(meth)acrylate, which are polyfunctional monomers, together with one or a combination of a plurality of curable monofunctional monomers and polyfunctional monomers, which have a hydrophilicity or no hydrophilicity.

Examples of monofunctional monomers include: 2-hydroxyethyl acrylate (HEA), 2-hydroxypropyl acrylate (HPA), 2-hydroxyethyl methacrylate (HEMA), styrene monomers, ethyl acrylate, and butyl acrylate.

Examples of polyfunctional monomers include: polyfunctional (meth)acrylate monomers, polyfunctional (meth) acrylic urethane monomers, and oligomers of these.

In some aspects, polymerization can be performed by, for example, thermal polymerization or photopolymerization but the polymerization is not limited to these. In the case of the thermal polymerization, a thermal polymerization initiator can be used. As the thermal polymerization initiator, for example, a hydrophilic thermal polymerization initiator can be used, such as a peroxide (e.g., potassium peroxodisulfate, ammonium peroxodisulfate) or an azo compound (e.g., VA-044, V-50, V-501, VA-057 (Wako Pure Chemical Industries, Ltd.)) can be used but the thermal polymerization initiator is not limited to these. In addition, for example, a radical initiator having a polyethylene oxide chain can also be used. As the catalyst, for example, N,N,N',N'-tetramethylethylene diamine and .beta.-dimethylaminopropionitrile, which are tertiary amine compounds, can be used.

In some aspects, photopolymerization is performed by, for example, using an ionizing radiation, such as electron beam and ultraviolet light. In the case where an electron beam is used, no photopolymerization initiator may be used; however, in the case of photopolymerization by ultraviolet light, a photopolymerization initiator is used. As the photopolymerization initiator, for example, a water soluble or hydrophilic photopolymerization initiator, such as Irgacure™ 2959, Darocur™ 1173, Darocur™ 1116, and Irgacure™ 184 (available from BASF), and Quantacure™ ABQ, Quantacure™ BT, and Quantacure™ QTX (available from Shell Chemicals), can be used but the photopolymerization initiator is not limited to these.

The thickness of the adhesive layer is not particularly limited. However, in some aspects, the thickness is about 10 μm to about 1,000 μm including for example, about 50 μm to about 500 μm, about 50 μm to about 250 μm, and about 50 μm to about 200 μm. In some aspects, the thickness is about 10 μm to about 500 μm including for example, about 50 μm to about 250 μm, and about 50 μm to about 200 μm. In some aspects, the thickness is between about 0.02 mm and about 0.25 mm, or about 0.09 mm and about 0.11 mm. In one aspect, the thickness is about 0.1 mm.

In one aspect, the substrate layer and the top layer include a polycarbonate and the adhesive layer is a pressure-sensitive adhesive layer.

In some aspects, the adhesive layer is a pressure-sensitive adhesive layer that is cured via treatment with heat. In one aspect, the adhesive layer is subject to pressure by laminating the substrate layer, adhesive layer and top layer together to form a composite laminate and subjecting the composite laminate to heat for a duration of time. In some aspects, laminating includes applying a compressive force to the adhesive layer via application of opposing forces to the substrate layer and the top layer. As will be appreciated, that this can be accomplished by any number of techniques known in the art, such as via mechanical rollers or other means of compressing the adhesive layer between the substrate layer and the top layer.

In some aspects, the microfluidic device of the disclosure is generated by forming a composite laminate including the substrate layer, adhesive layer and top layer and subsequently curing the composite laminate. In one aspect, the process includes laminating the adhesive layer and the top layer together to form an intermediate laminate, and bonding the intermediate laminate to the substrate layer to form the composite laminate. In one aspect, the process includes laminating the adhesive layer and the substrate layer together to form an intermediate laminate, and bonding the intermediate laminate to the top layer to form the composite laminate. In one aspect, bonding of the intermediate laminate to the substrate layer or top layer is accomplished by applying external pressure to the composite laminate. However, it will be appreciated that bonding may include chemical treatment or other bonding technique known in the art.

In some aspects, the microfluidic device is generated by forming a composite laminate including the substrate layer, pressure-sensitive adhesive layer and top layer and subsequently curing the composite laminate. In one aspect, the process includes laminating the pressure-sensitive adhesive layer and the top layer together to form an intermediate laminate, and bonding the intermediate laminate to the substrate layer to form the composite laminate. In one aspect, the process includes laminating the pressure-sensitive adhesive layer and the substrate layer together to form an intermediate laminate, and bonding the intermediate laminate to the top layer to form the composite laminate. Bonding of the intermediate laminate to the substrate layer or top layer is accomplished by applying external pressure to the composite laminate to depress the pressure-sensitive adhesive layer between the substrate layer and the top layer.

In some aspects, once formed, the composite laminate including the pressure-sensitive adhesive layer is cured by heat treatment. In various aspects, heat treatment includes subjecting the composite laminate to an elevated temperature for a duration of time. In some aspects, the elevated temperature is greater than about 25, 30, 35, 40, 45 or 55° C., including about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60° C. In some aspects, the composite laminate is subjected to the elevated temperature for at least about 24 hours and less than about 36 hours. In some aspects, the composite laminate is subjected to the elevated temperature for less than about 24, 20, 16, 12, 8 or 4 hours.

As shown in the Figures, in various aspects, the microfluidic device is planar in shape and has a length L, a width W and a thickness T. In some aspects, the dimension of the length L and the width W may be the same or the dimension of the length L may be greater than the width W. In some aspects, the dimension of the thickness T is smaller than the dimension of the length L and the width W. In some aspects, the dimension of the thickness T is greater than the dimension of the length L and/or the width W.

In some aspects as discussed herein, the lamination process can cause temporary compression of the layers in which the adhesive layer is compressed from a first thickness to a second reduced thickness less than the first thickness. In various aspects, the change in thickness is remediated via the curing process to produce a laminate structure having a stable and uniform thickness over the entire length L and width W of the planar device. In various aspects, the deviation from the uniform thickness of the laminated and cured device is less than about 10, 9, 8, 7, 6, 5, 4, 3, 2 or 1 µm over the entire length L and width W of the planar device. In some aspects, the deviation from the uniform thickness of the laminated and cured device is less than about 0 to about 5 µm, about 0 to about 4 µm, about 0 to about 3 µm, about 0 to about 2 µm, about 0 to about 1 µm, over the entire length L and width W of the planar device.

In some aspects, the first thickness is larger than or equal to the second thickness. In some aspects, the first thickness is less than or equal to the second thickness. In some aspects, the first thickness is less than or equal to the third thickness. In some aspects, the first thickness is greater than or equal to the third thickness. In some aspects, the first thickness is greater than or equal to the second thickness and the third thickness. In some aspects, the first thickness and the second thickness are greater than or equal to the third thickness. In some aspects, the second thickness is the same as the third thickness and optionally the first thickness. In some aspects, the second thickness is less than or equal to the first thickness and greater than or equal to the third thickness. In some aspects, the second thickness is less than or equal to the first thickness and less than or equal to the third thickness. In some aspects, the first thickness is greater than or equal to the second thickness, the second thickness is less than or equal to the third thickness, and the first thickness is greater than or equal to the third thickness. In some aspects, the first thickness is greater than or equal to the second thickness, the second thickness is less than or equal to the third thickness, and the first thickness is less than or equal to the third thickness. In some aspects, the first thickness is greater than or equal to the second thickness, the second thickness is less than or equal to the third thickness, and the first thickness is greater than or equal to the third thickness.

In various aspects, the deviation of the uniform thickness of the cured adhesive layer is less than about 10, 9, 8, 7, 6, 5, 4, 3, 2 or 1 µm over the entire length L and width W of the planar device. In some aspects, the deviation of the uniform thickness of the cured adhesive layer is less than about 0 to about 5 µm, about 0 to about 4 µm, about 0 to about 3 µm, about 0 to about 2 µm, about 0 to about 1 µm, over the entire length L and width W of the planar device.

In various aspects, the deviation of the uniform height of the one or more flow channels is less than about 10, 9, 8, 7, 6, 5, 4, 3, 2 or 1 µm over the entire dimension of the flow channels. In some aspects, the deviation of the uniform height is less than about 0 to about 5 µm, about 0 to about 4 µm, about 0 to about 3 µm, about 0 to about 2 µm, about 0 to about 1 µm, over the entire dimension of the flow channels.

In addition to producing a microfluidic device having a uniform thickness, the device of the present disclosure exhibits high dimensional stability which results, in part, from the curing process. It will be appreciated that the device is dimensionally stable over all structural features of the device, including for example, length, width, thickness, channel width, channel height, and the like. In various aspects, the structural dimensions of the device of the disclosure remain unchanged after the device is cured, for greater than about 5, 10, 15 or 20 years.

In various aspects, the microfluidic device is a planar device composed of at least three planar layers, e.g., a substrate layer, a top layer, and an adhesive layer including at least one channel or recess feature and being interposed between the substrate layer and the top layer.

Figure 1:
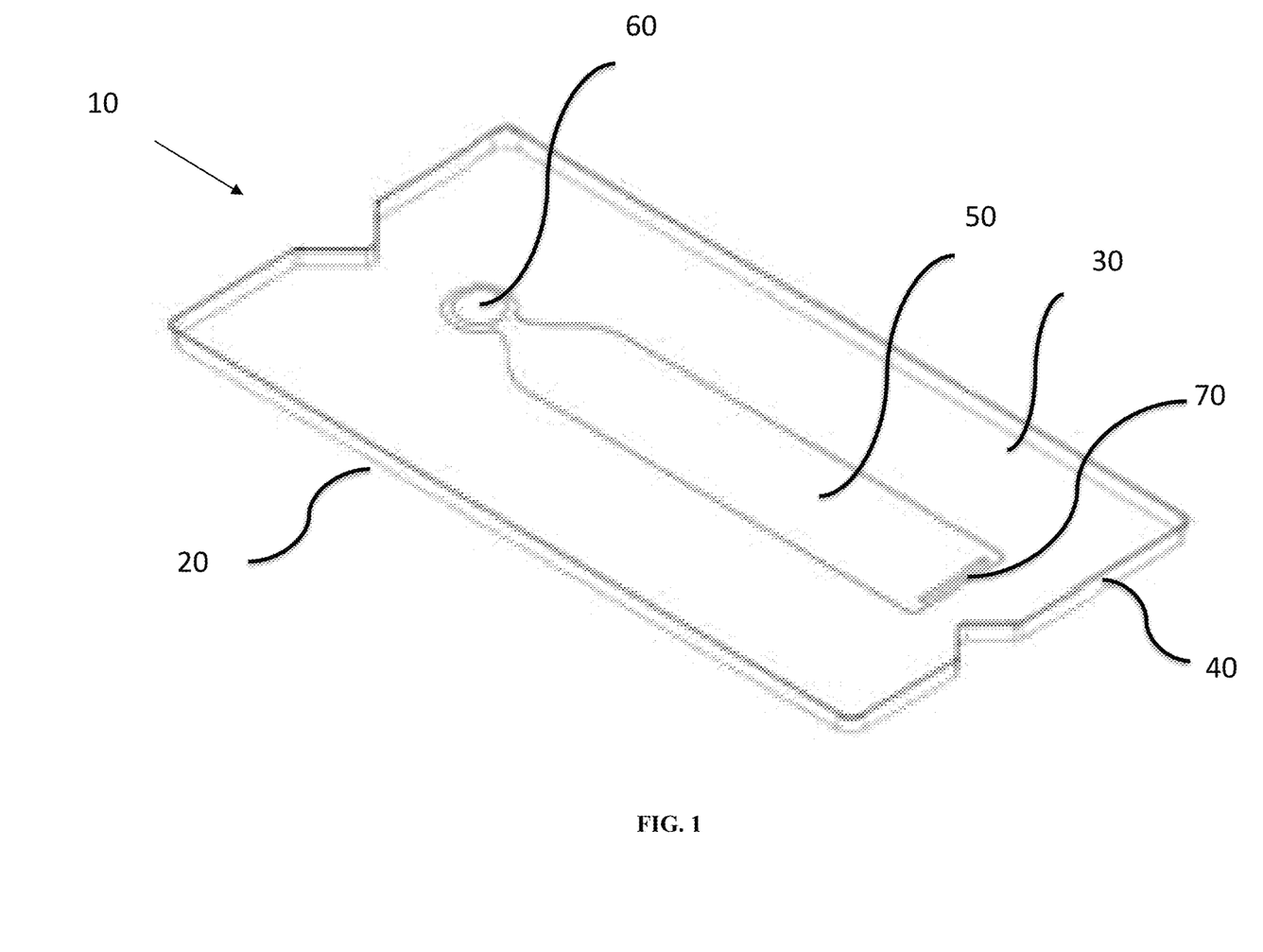
FIG. 1 is a perspective view of a laminate microfluidic device manufactured by the method described herein in one aspect of the disclosure.
Figure 2:
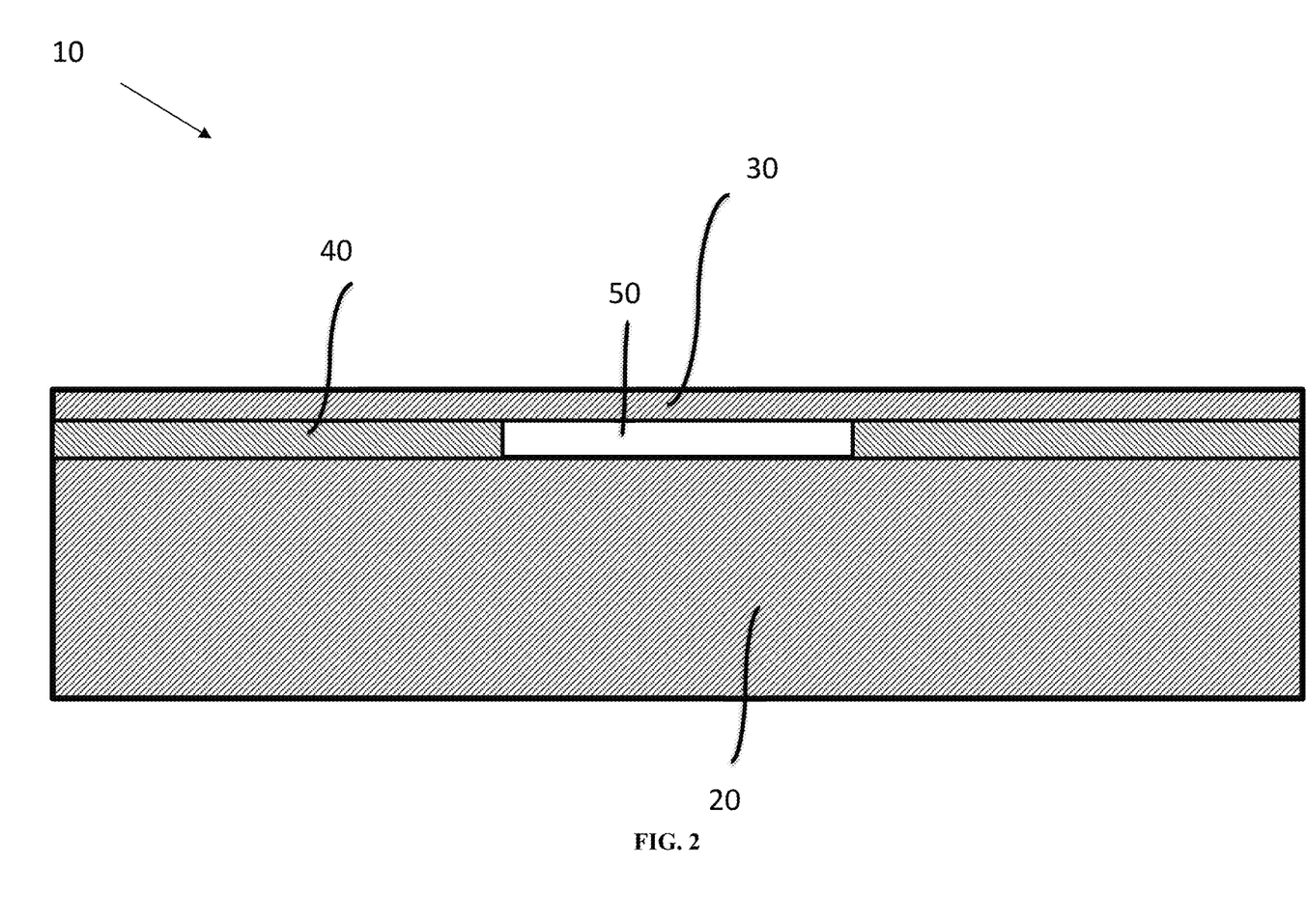
FIG. 2 is a cross-sectional view of the device depicted in FIG. 2 across the width of the device through the flow channel showing the device wherein the planar substrate is formed from three material layers with the flow channel being formed by laminating the three material layers.
Figure 3:
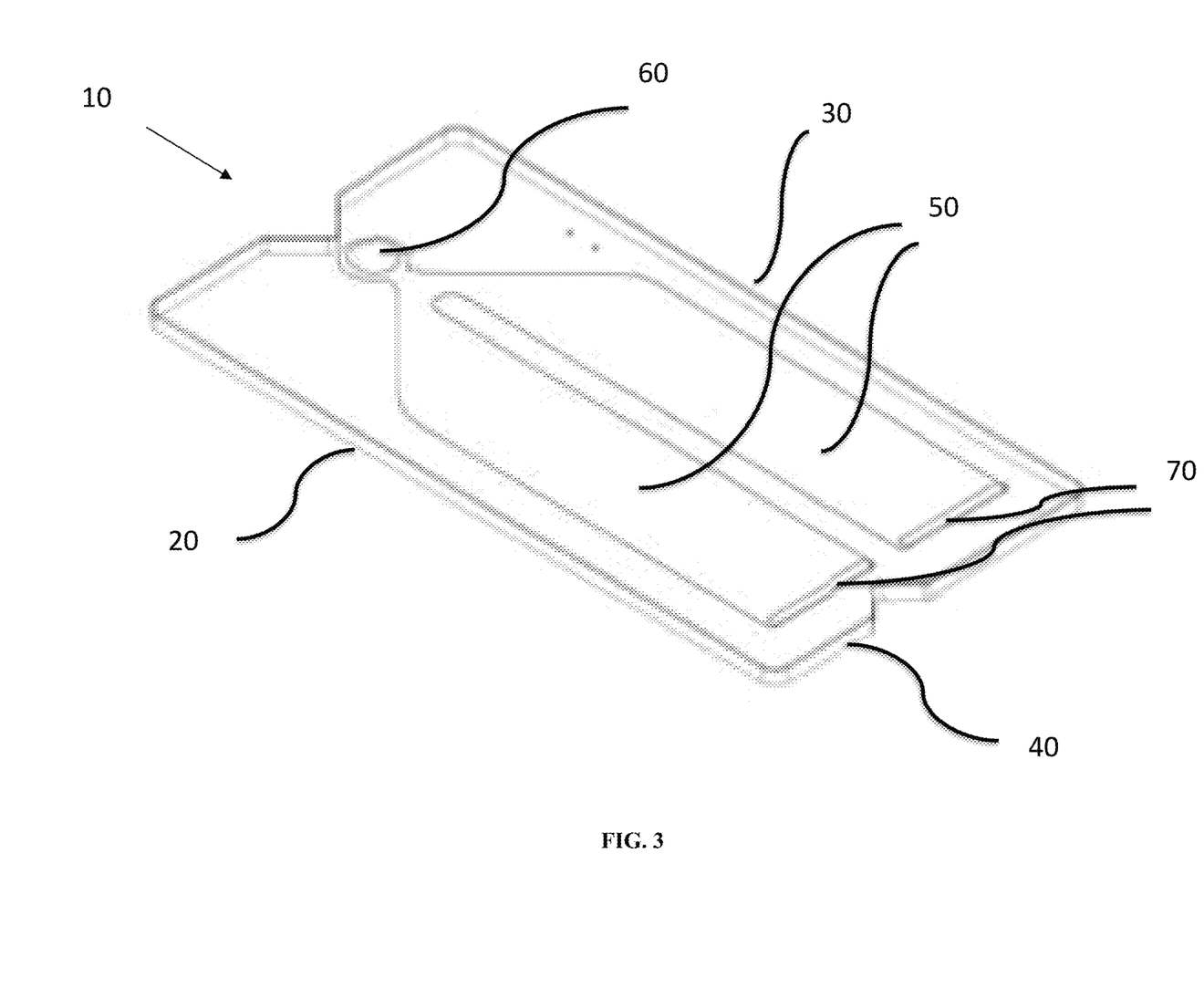
FIG. 3 is a perspective view of a laminate microfluidic device manufactured by the method described herein in one aspect of the disclosure.
Figure 4:
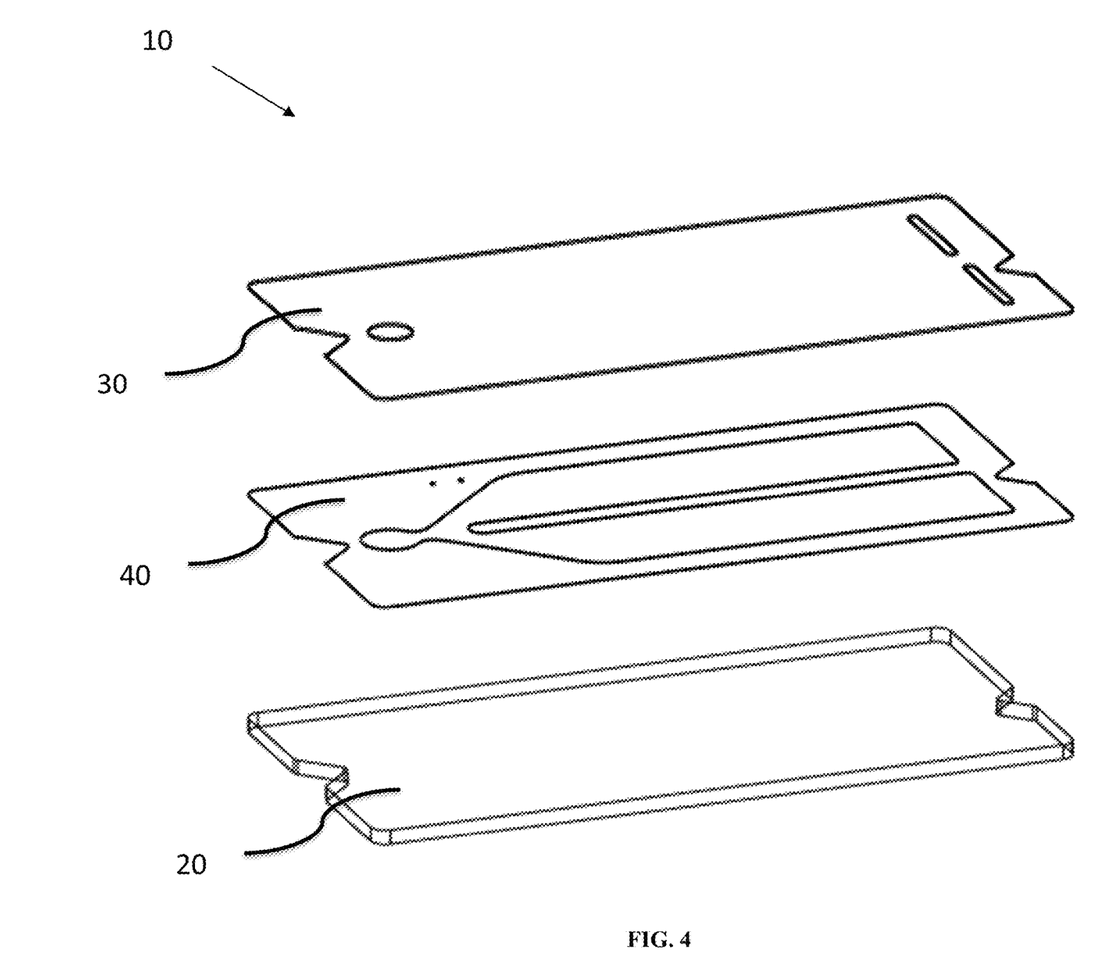
FIG. 4 is an exploded perspective view of the device depicted in FIG. 3 showing three individual material layers.
Figure 5A:
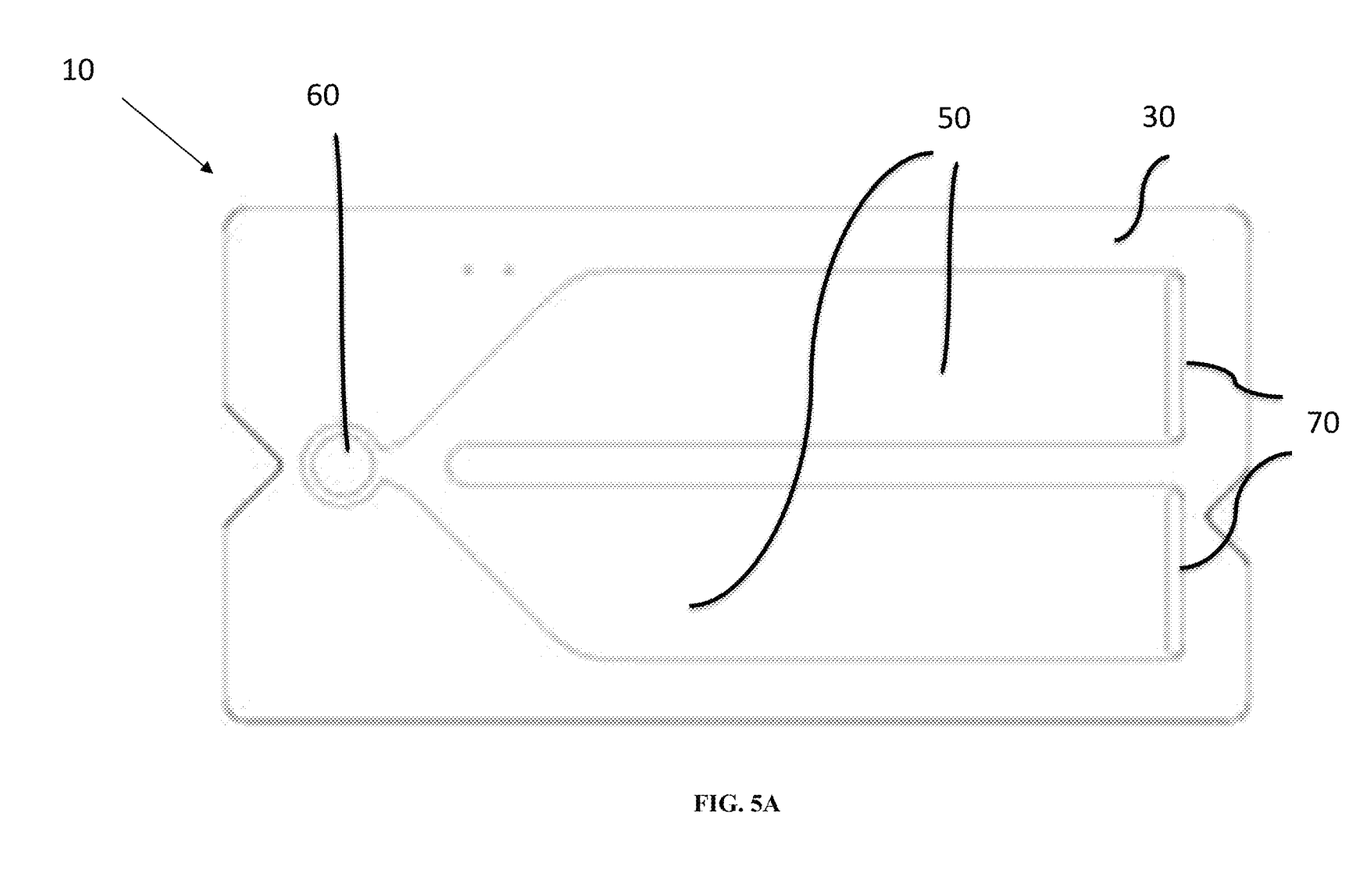
FIGS. 5A and 5B are a top-down view and a cross-sectional view, respectively, of the device depicted in FIG. 3.
Figure 5B:
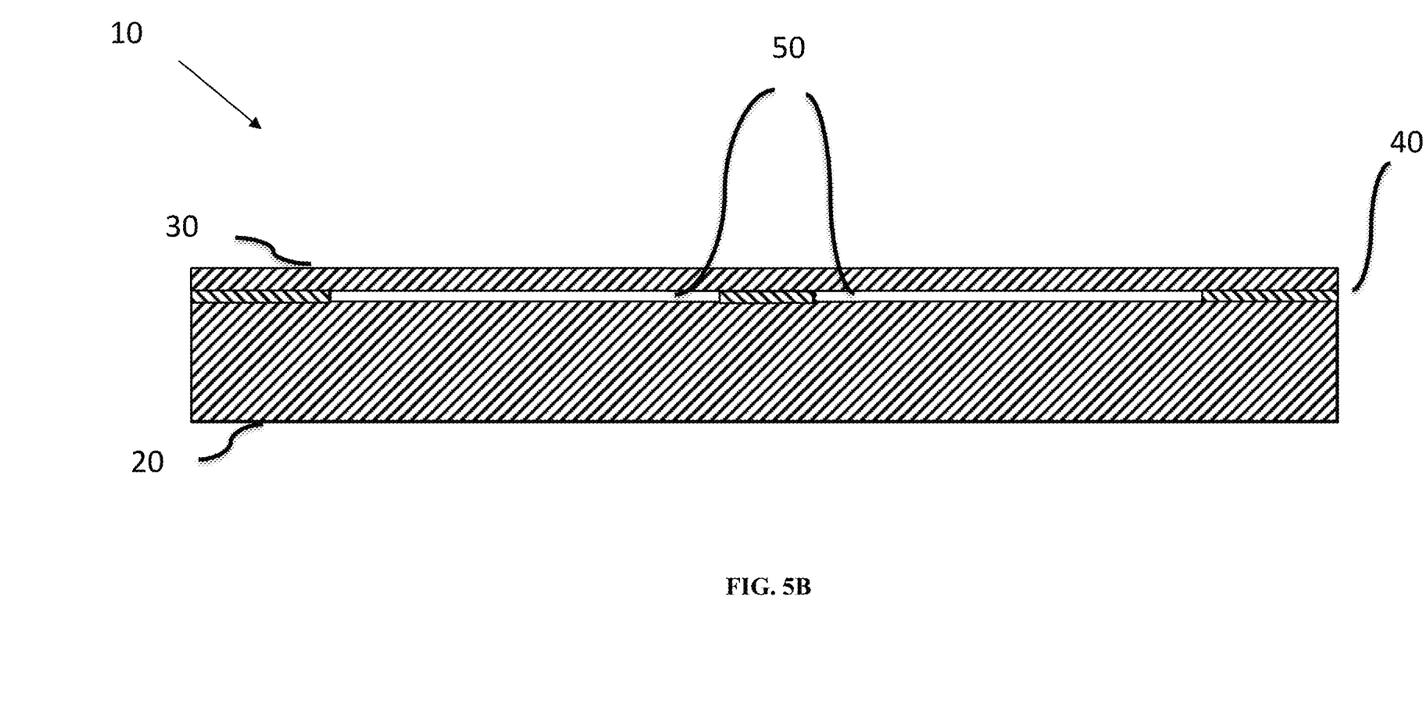
Figure 6:
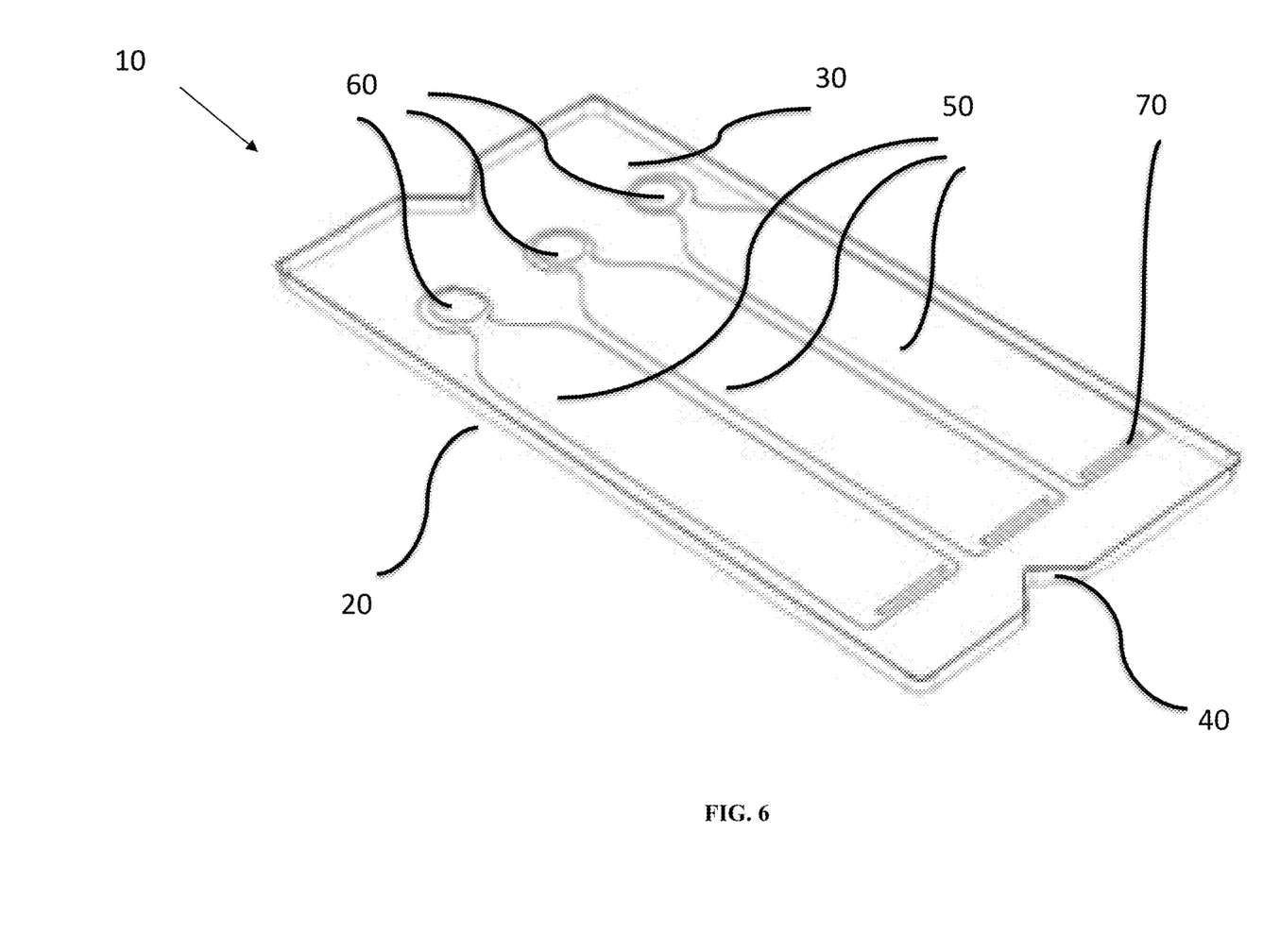
FIG. 6 is a perspective view of a laminate microfluidic device manufactured by the method described herein in one aspect of the disclosure.

As illustrated in FIGS. 1-6, the microfluidic device 10 includes at least one flow channel 50 formed in the adhesive layer 40. FIGS. 1-2 show a device 10 having one flow channel 50. FIGS. 3-5 show a device 10 have two flow channels 50. FIG. 6 shows a device 10 having three flow channels 50. While FIGS. 1-6 depict devices having flow channels, it will be appreciated that the device may include a variety of other features formed in the adhesive layer which are defined by a void of adhesive material between the substrate layer and top layer.

In certain aspects, the substrate layer and/or the top layer can be transparent or semitransparent and/or fluorescent to facilitate detection of analytes, for example by imaging. In some aspects, the device is configured to be imaged from the top.

In various aspects, the device may include a plurality of flow channels. For example, the device may include 2, 3, 4, 5, 6, 7, 8, 9, 10, 11, 12, 13, 14, 15, 16, 17, 18, 19, 20 or more flow channels. The flow channels may be arranged in any number of configurations with respect to one another. For example, the longitudinal axis of each flow channel may be arranged in parallel and extend along the length L of the device. Alternatively, the flow channels may be arranged in a radial manner extending from a central inlet in a spoke fashion. Alternatively, the flow channels may be arranged in a "binary tree" configuration. In some aspects, one or more of the flow channels intersect with one another at an acute, right or obtuse angle.

As shown in FIGS. 1-6, in some aspects, each flow channel is fluidly coupled to an inlet 60 and a vent 70. In some aspects, a flow channel 50 is fluidly coupled to a single inlet 60 and a single vent 70 which are not shared by another flow channel as shown in FIG. 1. In alternative aspects, multiple flow channels 50 share a single inlet 60 and each flow channel 50 is fluidly coupled to a different unshared vent 70 as shown in FIG. 3. In alternative aspects, multiple flow channels share a single vent and each flow channel is fluidly coupled to a different unshared inlet.

In various aspects, the device may include a plurality of vents, each being fluidly coupled to a single flow channel or a plurality of flow channels. In some aspects, a flow channel is fluidly coupled to a single vent. In alternative aspects, a flow channel is fluidly coupled to 2, 3, 4, 5, 6, 7, 8, 9, 10 or more vents.

A vent of the assay device may be disposed on the planar substrate in various locations. For example, a vent may be disposed in the top layer or the substrate layer of the device. Alternatively, a vent may be disposed in the adhesive layer, for example between the top layer and the substrate layer and aligned perpendicular to the thickness T of the device.

In various aspects, a channel or recess feature is formed in the adhesive layer before the adhesive layer is laminated to the top layer and/or substrate layer. For example, in some aspects, the channel or recess feature is formed in the adhesive layer and the adhesive layer is then laminated with the substrate layer and top layer to form a composite laminate. In this manner, a flow channel is formed in the device, wherein a top surface of the channel is defined by the top layer, a bottom surface of the channel is defined by the substrate layer, and side surfaces of the channel are defined by the adhesive layer. In various aspects, the device may include any number of flow channels through which fluid flow is directed during use of the device, for example to perform an assay. Additionally, the flow channels may be arranged in any pattern suitable to conduct a given assay.

One of skill in the art would appreciate that flow channels or recess features may be formed in the adhesive layer using a variety of techniques known in the art. In some aspects, the channels or recess features are formed by laser cutting, dye cutting, knife cutting, press cutting, etching, or mechanical or chemical milling.

There are several parameters that impact flow of a liquid sample through a flow channel. By way of example, some parameters include: dimensions and configuration of the flow channels, surface energy of the surfaces of the flow channels, degree of hydrophobicity or hydrophilicity of the surfaces of the flow channels, inclusion of functionalized coatings on the surfaces of the flow channels, and inclusion of texturization or microscopic patterning on the surfaces of the flow channels. It is envisioned that surfaces of the device of the present disclosure may by modified to control any combination of these parameters.

In some aspects, enhanced utility is achieved by applying hydrofluidic coatings to the device components prior to or after assembly. In the case of hydrofluidic coatings, the capillary force-driven fill properties of the device are enhanced to promote repeatable transport of fluid introduced into a flow channel throughout the entire channel structure.

As such, in some aspects, one or more surfaces of the planar substrate, such as an internal surface of the flow channel, may be treated to alter surface energy and consequently the degree of adhesion of an analyte with the surface. In some aspects, a surface is coated to increase hydrophilicity of the substrate surface to ensure a desired flow rate. In some aspects, a surface is coated to increase hydrophilicity of the substrate surface to ensure a predictable distribution of fluid constituents, such as cells, solids, molecules, particles and the like. In one aspect, a surface is coated to increase hydrophilicity of the substrate surface to ensure a desired flow rate and generation of a single monolayer of cells. In some aspects, a surface is coated to decrease hydrophilicity of the substrate surface to ensure a desired flow rate. In some aspects, a surface is coated to decrease hydrophilicity of the substrate surface to ensure a predictable distribution of fluid constituents, such as cells, solids, molecules, particles and the like. In one aspect, a surface is coated to decrease hydrophilicity of the substrate surface to ensure a desired flow rate and generation of a single monolayer of cells.

In some aspects, one or more surfaces of the device, such as a surface of the flow channel, may be functionalized. A surface may be referred to as "functionalized" when it includes a linker, a scaffold, a building block, or other reactive moiety attached thereto, whereas a surface may be "nonfunctionalized" when it lacks such a reactive moiety attached thereto.

A functionalized surface may refer to a surface having a functional group. A functional group may be a group capable of forming an attachment with another functional group. For example, a functional group may be biotin, which may form an attachment with streptavidin, another functional group. Exemplary functional groups may include, but are not limited to, aldehydes, ketones, carboxy groups, amino groups, biotin, streptavidin, nucleic acids, small molecules (e.g., for click chemistry), homo- and hetero-bifunctional reagents (e.g., N-succinimidyl (4-iodoacetyl) aminobenzoate (STAB), dimaleimide, dithio-bis-nitrobenzoic acid (DTNB), N-succinimidyl-S-acetyl-thioacetate (SATA), N-succinimidyl-3-(2-pyridyldithio) propionate (SPDP), succinimidyl 4-(N-mafeimidomethyl)-cyclohexane-1-carboxylate (SMCC) and 6-hydrazinonicotimide (HYNIC), and antibodies. In some instances, the functional group is a carboxyl group (e.g., COOH).

In various aspects, one or more surfaces may be treated or coated to render the surface hydrophilic or hydrophobic. A variety of surface treatments and surface modification techniques may be used to alter the properties of the surface. Examples include, but are not limited to, oxygen plasma treatments to render hydrophobic material surfaces more hydrophilic, the use of wet or dry etching techniques to smooth (or roughen) silicon surfaces, adsorption and/or grafting of polyethylene oxide or other polymer layers to substrate surfaces to render them more hydrophilic and less prone to non-specific adsorption of biomolecules and cells, the use of silane reactions to graft chemically-reactive functional groups to otherwise inert silicon surfaces. Photodeprotection techniques can be used to selectively activate chemically-reactive functional groups at specific locations of the surface, for example, the selective addition or activation of chemically-reactive functional groups such as primary amines or carboxyl groups on the surface may be used to covalently couple oligonucleotide probes, peptides, proteins, or other biomolecules to the surface. In general, the choice of surface treatment or surface modification utilized will depend on one or more of the type of surface property that is desired, the type of material from which the non-adhesive layer is made, and the type of material from which the adhesive layer is made depending on whether the adhesive layer is laminated to the non-adhesive layer before or after the surface is treated or otherwise modified.

With regard to hydrophilicity of a surface, one or more surfaces may be treated or coated to reduce the contact angle of a liquid sample on the surface to about 90 degrees or less. In some aspects, the hydrophilicity of a surface is increased such that the contact angle of the surface is less than about 85, about 80, about 75, about 70, about 65, about 60, about 55, about 50, about 45, about 40, about 35, about 30, about 25, about 20, about 15 or about 10 degrees. In some aspects, the hydrophilicity of the bottom surface of the flow channel is increased such that the contact angle of the surface is less than about 85, about 80, about 75, about 70, about 65, about 60, about 55, about 50, about 45, about 40, about 35, about 30, about 25, about 20, about 15 or about 10 degrees. This improves flow of liquid sample through the flow channel and reduces the risk of air bubble formation and entrapment.

The functional groups on a surface may be different for different regions of the surface. The functional groups on the surface may be the same for all regions of the surface. For example, the entire internal surface of the flow channel may include the same functional group. Alternatively, different regions of the internal surface of the flow channel may include different functional groups.

Addition of functional groups to a surface may be utilized to form capture regions on the surface to immobilize or bind an analyte. In this manner, a specific analyte may be concentrated at a specific region of the surface to increase detection and/or analysis of the analyte. This can also be accomplished by texturizing the surface or including microscopic structures which may also be used utilized to inhibit or reverse agglomeration of analytes.

In some aspects, the depth and/or height of a flow channel is substantially uniform throughout the entire channel. In alternative aspects, the depth of a flow channel varies across an individual channel. In aspects in which the assay device includes multiple flow channels, all of the flow channels may have the same depth, or each flow channel may have a different depth with respect to one another.

In various aspects, the width of the flow channels can be from about 5 µm to about 1000 µm and, for larger width flow channels, can be about 100 µm, at or between about 100 µm and about 150 µm, at or between about 150 µm and about 200 µm, at or between about 200 µm and about 250 µm, at or between about 250 µm and about 300 µm, at or between about 300 µm and about 350 µm, at or between about 350 µm and about 400 µm, at or between about 400 µm and about 450 µm, at or between about 450 µm and about 500 µm, at or between about 500 µm and about 550 µm, at or between about 550 µm and about 600 µm, at or between about 600 µm and about 650 µm, at or between about 650 µm and about 700 µm, at or between about 700 µm and about 750 µm, at or between about 750 µm and about 800 µm, at or between about 800 µm and about 850 µm, at or between about 850 µm and about 900 µm, at or between about 900 µm and about 950 µm, at or between 950 µm and about 1000 µm. In some applications, a range of flow channel widths is from about 75 µm to about 125 µm. However, in certain instances, channel widths could exceed 1000 µm. For example, in some aspects, the width of the flow channel is equal to or greater than about 1000 µm, 1500 µm, 2000 µm, 2500 µm, 3000 µm, 3500 µm, 4000 µm, 4500 µm, 5000 µm, 5500 µm, 6000 µm, 6500 µm, 7000 µm, 7500 µm, 8000 µm, 8500 µm, 9000 µm, 9500 µm, 10000 µm, 10500 µm, 11000 µm, 12000 µm, 15000 µm, 20000 µm, 30000 µm, 50000 µm, or 100000 µm. For narrower channels, the widths can be about 5 µm or greater and about 100 µm or smaller. Channel widths can be from about 10 µm to about 75 µm, from about 15 µm to about 50 µm, and from about 20 µm to about 40 µm. In some aspects, the channel width is about 5, 10, 15, 20, 25, 30, 35, 40, 45, 50, 55, 60, 65, 70, or 75 µm.

In some aspects, the channel height can be from about 5 µm to about 100 µm, from about 10 µm to about 75 µm, from about 15 µm to about 50 µm, and from about 20 to about 40 µm. In some aspects, the channel height is about 5, 10, 15, 20, 25, 30, 35, 40, 45, 50, 55, 60, 65, 70, or 75 µm. In some aspects, the cross-sectional area can be from about 20 to about 13000 µm2, from about 50 to about 10000 µm2, from about 200 to about 8000 µm2, from about 250 to about 5000 µm2, from about 500 to about 3000 µm2, and in many aspects, it is from about 1400 to about 1600 µm2. In some aspects, the cross-sectional area is about 500, 600, 700, 800, 900, 1000, 1100, 1200, 1300, 1400, 1500, 1600, 1700, 1800, 1900, or about 2000 µm2. In some aspects, the cross-sectional area is equal to or greater than about 1000, 5000, 10000, 50000, 100000, 2000000, 300000, 400000, 500000, 600000, 700000, 800000, 900000, or 1000000 µm2.

In some aspects, the height of a flow channel can be between about 0.02 and about 0.25 mm, inclusive. In some aspects, the height can be between about 0.1 and about 0.15 mm, inclusive. In some aspects, the height is about 0.02, about 0.03, about 0.04, about 0.05, about 0.06, about 0.07, about 0.08, about 0.09, about 0.1, about 0.11, about 0.12, about 0.13, about 0.14, about 0.15, about 0.16, about 0.17, about 0.18, about 0.19, about 0.20, about 0.21, about 0.22, about 0.23, about 0.24 or about 0.25 mm. In some aspects, the height is between about 0.08 and about 0.12 mm, including about 0.08, about 0.09, about 0.1, about 0.11 or about 0.12 mm.

In various aspects, the shape of the cross-section of individual channels can be the same or different. In some aspects, the shape of the cross-section of individual channels can take different shapes such as square, rectangular, other polygonal, circular, elliptical, semicircular, semielliptical, and the like. Additionally, the cross-sectional shapes and areas can vary within the same channel.

In various aspects, the microfluidic device is configured to perform an assay to detect an analyte present in a liquid sample. In some aspects, the analyte is a cell, or portion thereof, or cellular nuclei, or portion thereof. In some aspects, the analyte is a biomolecule such as a nucleic acid, amino acid, protein, peptide, hormone, steroid, lipid, or carbohydrate. In some aspects, the analyte is a chemical compound such as a small organic molecule. In some aspects, the analyte is a microorganism, such as a bacterium, virus, or portion thereof.

In various aspects, the microfluidic device may be configured to utilize any type of liquid sample, so long as the sample is capable of fluid flow along a flow channel, either passively or by applied force. It will be appreciated that flowability of a liquid sample may be altered by dilution or concentration of the sample. Further, a solid or otherwise non-flowable sample may be converted to a liquid sample by any method known in the art. Additionally, the sample may be treated with a reagent to alter a property of the sample before being applied to the microfluidic device. In one aspect, the liquid sample is a biological fluid. By way of example, a biological fluid may include, but is not limited to amniotic fluid, aqueous humour, vitreous humour, blood, whole blood, fractionated blood, plasma, serum, breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, prostatic fluid, nipple aspirate fluid, lachrymal fluid, perspiration, cheek swabs, cell lysate, gastrointestinal fluid, biopsy fluid and urine. In one aspect, the biological fluid is whole blood.

In some aspects the device is configured to receive a liquid sample and generate a monolayer of components of one or more analytes present in the liquid sample. For example, the device is configured to receive a whole blood sample, optionally at a specified dilution and generate a monolayer of cells for analysis and/or detection using a technique such as imaging. To facilitate image analysis of the cellular components, the whole blood sample may be stained with a fluorescent dye or processed in another way prior to input into the device.

Generating a "monolayer," e.g., a single layer of components of a liquid sample can facilitate detection of analytes present in the sample. For example, generating a monolayer of components of a whole blood sample can facilitate imaging and counting of cellular components, e.g., red blood cells, white blood cells, and platelets, within the whole blood sample.

In various aspects, the device of the present disclosure is operable to perform a target hematology assay including, but not limited to, any of a hematocrit determination, a red blood cell count, a platelet count, a white blood cell count, or a white blood cell differential.

For example, in some aspects, the device is configured to generate a single layer of blood cells across the one or more channels for imaging purposes to support complete blood count analysis. In this aspect, consistent fill properties are essential to ensure that fluid propagates through the structure at a predictable rate to produce a roughly homogeneous distribution of cells. A flow rate that is too fast tends to create trapped air bubbles that reduce usable fields of view and analytical accuracy, while a flow rate that is too slow yields a non-homogenous distribution of cells where the solids separate from the plasma prior to complete fill of the channel structure (also reducing analytical accuracy). Normally, driving a consistent flow rate through a microfluidic structure requires an active system that pumps fluid through channel structures of the device. In some aspects, the device of the disclosure utilizes a combination of repeatable channel geometry achieved by the method of the disclosure and hydrophilic surface coatings to accomplish analytical repeatability with both a simple microfluidic consumable and a system with reduced cost/complexity.

It is to be noted that while this disclosure discloses use of imaging to detect an analyte in a liquid sample, other types of detection methods may be utilized in addition to imaging or in the alternative.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. For example, while the current subject matter is described as being used in connection with optical analytical devices and systems, it will be appreciated that the devices, components and systems described herein can be used with other types of analytical devices and systems, or in any technological field that utilizes bonded plastics. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results.

Although the invention has been described with reference to the above examples, it will be understood that modifications and variations are encompassed within the spirit and scope of the invention.

What is claimed is:

1. A laminate microfluidic device comprising
a substrate layer;
an adhesive layer having at least one channel or recess feature, the adhesive layer comprising a cured adhesive, the adhesive layer having a stable and uniform thickness across an entire width and length of the device of less than about 5 µm;
a top layer laminated to the adhesive layer to form an intermediate laminate, the intermediate laminate bonded to the substrate layer to form a composite laminate.

2. The laminate microfluidic device of claim 1, wherein the adhesive layer has a thickness deviation of less than about 4, 3, 2 or 1 µm.

3. The laminate microfluidic device of claim 1, wherein the adhesive layer is composed of a silicone, cyanoacrylate, urethane, acrylic, epoxy or thermoplastic adhesive.

4. The laminate microfluidic device of claim 1, wherein the adhesive layer is composed of an acrylic pressure-sensitive adhesive having a base acrylic monomer.

5. The laminate microfluidic device of claim 1, wherein the substrate layer and/or the top layer comprises an electrically conductive material.

6. The laminate microfluidic device of claim 1, wherein the substrate layer and/or the top layer comprises electronic circuitry.

7. The laminate microfluidic device of claim 6, wherein the substrate layer and/or the top layer comprises one or more electrodes.

8. The laminate microfluidic device of claim 6, wherein the substrate layer and/or the top layer is a printed circuit board.

9. The laminate microfluidic device of claim 1, wherein the substrate layer and/or the top layer is optically transparent or semi-transparent.

10. The laminate microfluidic device of claim 1, wherein a top surface of the substrate layer and/or a bottom surface of the top layer comprises a functionalized coating or is texturized.

11. The laminate microfluidic device of claim 1, wherein the composite laminate comprises a polymerized monomer.

12. The laminate microfluidic device of claim 1, wherein the substrate layer and/or the top layer is composed of glass, silicon, ceramic, metal, polymer, or a combination thereof.

13. The laminate microfluidic device of claim 1, wherein the top layer further comprises a vent.

14. The laminate microfluidic device of claim 1, wherein the at least one channel or recess feature comprises a first channel and a second channel wherein the first channel and second channel have a different depth with respect to one another.

15. The laminate microfluidic device of claim 1, wherein the at least one channel or recess feature comprises a first channel wherein the first channel height is configured to allow uniform flow of fluid and analyte within the first channel.

16. The laminate microfluidic device of claim 1, wherein the at least one channel or recess feature comprises sample for target analyte detection.

17. A laminate microfluidic device comprising:
a substrate layer;
a cured adhesive layer with a stable and uniform thickness and having a first channel and a second channel;
a top layer, the substrate layer, top layer and adhesive layer forming a composite laminate.

18. The laminate microfluidic device of claim 17, wherein the cured adhesive layer has a stable and uniform thickness across an entire width and length of the device, the stable and uniform thickness having a thickness deviation of less than about 5 µm.

19. The laminate microfluidic device of claim 17, wherein the cured adhesive layer is interposed between two non-adhesive layers.

20. A microfluidic device comprising:
an intermediate laminate layer comprising a cured adhesive layer laminated to a top layer, the adhesive layer comprising at least one channel or recess feature; and
the intermediate laminate bonded to a substrate layer.

* * * * *